United States Patent [19]

Middendorf et al.

[11] Patent Number: 5,230,781
[45] Date of Patent: Jul. 27, 1993

[54] SEQUENCING NEAR INFRARED AND INFRARED FLUORESCENCE LABELED DNA FOR DETECTING USING LASER DIODES

[75] Inventors: Lyle R. Middendorf, Lincoln, Nebr.; Gabor Patonay, Stone Mountain, Ga.

[73] Assignee: Li-Cor, Inc., Lincoln, Nebr.

[21] Appl. No.: 763,230

[22] Filed: Sep. 20, 1991

Related U.S. Application Data

[60] Continuation-in-part of Ser. No. 570,503, Aug. 21, 1990, which is a continuation-in-part of Ser. No. 78,279, Jul. 27, 1987, which is a division of Ser. No. 594,676, Mar. 29, 1984, Pat. No. 4,729,947.

[51] Int. Cl.⁵ ............... G01N 27/26; B01D 57/02
[52] U.S. Cl. ..................... 204/182.8; 204/299 R; 356/347
[58] Field of Search ............. 204/182.8, 299 R; 356/344

[56] References Cited

U.S. PATENT DOCUMENTS

| | | | |
|---|---|---|---|
| 4,116,565 | 9/1978 | Powell et al. | 356/344 |
| 4,675,095 | 6/1987 | Kambara et al. | 356/344 X |
| 4,707,235 | 11/1987 | Englert et al. | 204/299 R X |
| 4,832,815 | 5/1989 | Kambara et al. | 204/299 R |
| 4,874,492 | 10/1989 | Mackay | 204/299 R |
| 4,881,812 | 11/1989 | Ohkubo et al. | 204/299 R X |
| 4,971,677 | 11/1990 | Kambara et al. | 356/344 X |
| 5,051,162 | 9/1991 | Kambara et al. | 204/299 R |
| 5,062,942 | 11/1991 | Kambara et al. | 204/299 R |
| 5,069,769 | 12/1991 | Fujimiya et al. | 204/182.8 |

Primary Examiner—John Niebling
Assistant Examiner—John S. Starsiak, Jr.
Attorney, Agent, or Firm—Vincent L. Carney

[57] ABSTRACT

To sequence DNA automatically, DNA marked with near infrared fluorescent dyes are electrophoresed in a plurality of channels through a gel electrophoresis slab wherein the DNA samples are resolved in accordance with the size of DNA fragments in the gel electrophoresis slab into fluorescently marked DNA bands. The separated samples are scanned photoelectrically with a laser diode and a sensor, wherein the laser scans with scanning light at a scanning light frequency within the absorbance spectrum of said fluorescently marked DNA samples and light is sensed at the emission frequency of the marked DNA. The light is modulated from said laser at a predetermined modulation frequency and fluorescent light emitted by said DNA bands at said modulation frequency is detected, whereby background noise from the medium through which the light is transmitted is discriminated against.

7 Claims, 5 Drawing Sheets

SEQUENCING NEAR INFRARED AND INFRARED FLUORESCENCE LABELED DNA FOR DETECTING USING LASER DIODES

REFERENCE TO RELATED APPLICATIONS

This application is a continuation-in-part of application Ser. No. 07/570,503 filed Aug. 21, 1990, which is a continuation-in-part application of Ser. No. 07/078,279 filed Jul. 27, 1987, which is a division of U.S. application Ser. No. 594,676 for DNA SEQUENCING filed by Middendorf et al. on Mar. 29, 1984, and assigned to the same assignee as this application, now U.S. Pat. No. 4,729,947.

BACKGROUND OF THE INVENTION

This invention relates to the sequencing of fluorescence labeled DNA and the detecting of the DNA after irradiation by light from a laser.

In one class of techniques for sequencing DNA, identical strands of DNA are marked with fluorescent dye. The strands are marked by attaching specially synthesized fluorescent oligonucleotide primers to the strands of DNA.

The strands are separated into four aliquots. The strands in a given aliquot are either individually cleaved at or synthesized to any base belonging to only one of the four base types, which are adenine, guanine, cytosine and thymine (hereinafter A, G, C and T). The adenine-, guanine-, cytosine- and thymine- terminated strands are then electrophoresed for separation and the separated strands are irradiated by a laser and the emission detected. The rate of electrophoresis indicates the DNA sequence.

In a prior art sequencing technique of this class, the fluorescent dyes used as markers have their maximum emission spectra in the visible range, the DNA is subject to irradiation in the visible spectra, and visible spectra detectors and light sources are used. Generally photomultipliers tubes are used for detection.

The prior art techniques for DNA sequencing have several disadvantages such as: (1) because the dyes have their emission spectra in the visible light spectrum, the lasers used to excite the fluorescent markers and, under some circumstances, the detectors for the light tend to be expensive, such as for example, relatively large and expensive lasers are needed under some circumstances; and (2) they are relatively noisy.

SUMMARY OF THE INVENTION

Accordingly, it is an object of the invention to provide a novel technique for DNA sequencing.

It is a further object of the invention to provide novel apparatuses and methods for the sequencing of near infrared and infrared fluorescence labeled DNA and the detection of the DNA after irradiation by light from laser diodes.

It is a still further object of the invention to provide at least four novel dyes each of which fluoresces in the infrared or near infrared region, has a wavelength that is electronically distinguishable from the other three radiation wavelengths when attached to a DNA probe or primer and which can be attached to a DNA probe or primer.

It is a still further object of the invention to provide at least four novel dyes, each of which fluoresces in the infrared or near infrared region, has a wavelength that is electronically distinguishable from the other three radiation wavelengths when attached to an oligonucleotide and contains a functional group that can be used for attachment to an oligonucleotide.

It is a still further object of the invention to provide a novel probe or primer that contains a dye that fluoresces in the infrared or near infrared region.

It is a still further object of the invention to provide a technique for continuous sequencing of DNA.

It is a still further object of the invention to provide a novel technique for continuously sequencing DNA using fluorescent detection.

It is a still further object of the invention to provide a novel technique for DNA sequencing using a novel fluorescent marker fastened to the DNA.

It is a still further object of the invention to provide a novel technique for continuously sequencing DNA marked with fluorescence which more clearly distinguishes marked DNA fragments from background fluorescence.

It is a still further object of the invention to provide a novel fluorescent marker, method of synthesizing the marker and of attaching it to DNA.

It is a further object of the invention to provide a novel method, marker and equipment that permits the detection of marked molecules, including DNA, using diode light sources and detectors.

It is a further object of this invention to provide a novel fluorescent dye.

In accordance with the above and further objects of the invention, the sequencing of near infrared and infrared fluorescence labeled DNA and the detection of the DNA after irradiation by infrared or near infrared light from a laser diode is accomplished using a novel label. The strands of DNA are continuously electrophoresed and identified for any of several purposes, such as for example: (1) DNA sequencing; and (2) analysis of strands varying in length as prepared by such techniques as restriction enzyme cutting or polymerase chain reaction (PCR).

To aid in identification, the strands are marked with fluorescent labels that emit light in the infrared or near infrared region. The strands are irradiated with light in the infrared or near infrared region and the light emitted from the fluorescent labels is detected and used to obtain information about the DNA strands.

The marking is by direct labeling of fluorescent markers to the strands or by fluorescently labelled probes or primers hybridized to the separated strands. In one embodiment, the strands are detected by scanning with an infrared laser diode light source.

The scanning apparatus includes a laser diode that emits light of a wavelength near or in the optimum absorption spectrum of the marker. In the preferred embodiment, the light source is a diode laser that scans channels of DNA strands with infrared light having a wavelength that matches the absorbance region of the marker. The detector includes a light sensor which is preferably an avalanche photodiode sensitive to the near infrared light emission of the marker. It may include a filtering system having a band pass suitable for passing selectively the optimum emission of the fluorescent marker to the light sensor.

The photodiode, photomultiplier or other light detector selectively detects the fluorescence, using techniques which enhance the signal/noise ratio. One technique is to modulate the laser source by pulsing the electrical current driving the laser, with detection through a lock-in amplifier. The detection is made in a wavelength band including the high emission spectrum of the fluorescent marker.

To mark the DNA strand, a known infrared dye is modified to provide the desired wavelengths of maximum absorption and fluorescence. One such dye, the formula of which is shown in formula 1, with R being —$CH_2$—$CH_3$ is close to having the desired wavelength of maximum fluorescence and the wavelength of maximum absorbance may be modified by changing the functional group R. The unmodified dye may be obtained from Laboratory and Research Products Division, Eastman Kodak Company, Rochester, N.Y., 14650. It is advertised in Kodak publication JJ-169.

In the preferred embodiment, the fluorescence maximum wavelength is about 819 nanometers and the detector is adjusted to receive this wavelength and not others by appropriate filtering. The absorption maximum is selected to be different and to correspond to the preferred available laser diode emission. For example, in this formula, R may be any of the following four groups, depending on the desired wavelength of the absorbed light, which are:

(1) —$CH_2$—$CH_2$—OH for an excitation wavelength of 796 nanometers;

(2) —$CH_2$—$CH_2$—$CH_2$—OH for an excitation wavelength of 780 nanometers, which is the preferred embodiment;

(3) —$CH_2$—$CH_2$—$CH_2$—$CH_2$—$CH_2$—$CH_2$—OH for an excitation wavelength of 745 nanometers; and (4) —$CH_2$—$CH_2$—O—$CH_2$—$CH_2$—O—$CH_2$—O—$CH_2$—OH for an excitation wavelength of 790 nanometers.

In another embodiment, the infrared dye are selected to provide at least four dyes with each dye having its exitation and/or radiation spectra spaced sufficiently from each other dye so the flourescence from each dye can be electronically distinguished from each other dye either by the wavelength that excites it into fluorescence or the wavelength at which it fluoresces or both. The spacing is maintained sufficiently close to be excited by laser diodes. The functional groups may be modified as explained above for spacing between the absorption maxima and fluorescence maximum. The dyes may be incorporated in probes and primers for attachment to oligonucleotides as described in Ruth, Jerry L. (1984) DNA 3, 123. The —OH group provides appropriate linkage.

From the above summary, it can be understood that the techniques for the sequencing of fluorescence labeled DNA of this invention have several advantages, such as: (1) because the dyes have their emission spectra in the infrared or near infrared light spectrum, small inexpensive infrared diode lasers may be used; and (2) they are characterized by relatively low noise.

SUMMARY OF THE DRAWINGS

The above noted and other features of the invention will be better understood from the following detailed description when considered with reference to the accompanying drawings in which.

DETAILED DESCRIPTION

The sequencing of near infrared and infrared fluorescence labeled DNA and the detection of the DNA after irradiation by infrared or near infrared light from a laser diode is accomplished using an infrared or near infrared label prepared for this purpose and either directly attached to the DNA or attached to probes or primers that will be attached to the DNA. The strands of DNA are continuously electrophoresed and identified for any of several purposes, such as for example: (1) DNA sequencing; and (2) analysis of strands varying in length as prepared by such techniques as restriction enzyme cutting or polymerase chain reaction (PCR).

The strands are marked with fluorescent labels that have their maximum fluorescense and their maximum absorbance at wavelengths of light in the infrared and near infrared region. The strands are irradiated with light in the infrared or near infrared region from a laser diode and the light emitted from the fluorescent labels is detected and used to obtain information about the DNA strands. The detector includes a light sensor which is preferably an avalanche photodiode sensitive to the near infrared light emission of the marker. It may include a filtering system having a band pass suitable for passing selectively the optimum emission of the fluorescent marker to the light sensor.

To mark the DNA strand, a known infrared dye is modified to provide the desired wavelengths of maximum absorption and fluorescence. There are many such dyes such as for example: (1) 3,3'-Diethylthiadicarbocyanine Iodide; (2) 3,3'-Diethylthiatricarbocyanine Perchlorate; (3) 3,3'Diethyloxatricarbocyanine Iodide; (4) 1,1',3,3,3'-Hexamethylindotricarbocyanine Perchlorate; (5) 1,1'-Diethyl-2,2'-dicarbocyanine Iodide; (6) 3,3'-Diethylthiadicarbocyanine Iodide; (7) 3,3'-Diethyloxatricarbocyanine Iodide; (8) 1,1',3,3,3',3'-Hex-

FORMULA 1 amethylindotricarbocyanine Perchlorate; (9) 1,1',3,3,3',3'-Hexamethylindotricarbocyanine Iodide; and (10) Indocyanine Green.

In the preferred embodiment, the dye has the formula shown in formula 1, with R being $-CH_2-CH_3$. This dye is close to having the desired wavelength of maximum fluorescence and the wavelength of maximum absorbance may be modified by changing the functional group R. The unmodified dye may be obtained from Laboratory and Research Products Division, Eastman Kodak Company, Rochester, N.Y. 14650. It is advertised in the Kodak laser dyes, Kodak publication JJ-169.

(1) $-CH_2-CH_2-OH$ for an emission wavelength of 796 nanometers;

(2) $-CH_2-CH_2-CH_2-OH$ for an emission wavelength of 780 nanometers, which is the preferred embodiment;

(3) $-CH_2-CH_2-CH_2-CH_2-CH_2-CH_2-OH$ for an emission wavelength of 745 nanometers;

(4) $-CH_2-CH_2-O-CH_2-CH_2-O-CH_2-O-CH_2-OH$ for an emission wavelength of 790 nanometers; and (5) $-CH_2-CH_2-SH$ for an emission wavelength of 810 nanometers.

EQUATION 1

The modifications can be made in a manner known in the art. For example, changes occur when different esters are formed replacing the ethyl alcohol in the original dye molecule (R equal $-CH_2-CH_3$ of formula 1). If different glycol esters are formed, absorption maxima of these new near infrared dyes shift to the longer wavelengths. Moreover, new dyes may be synthesized rather than modifying existing dyes in a manner known in the art.

The absorption maximum is dependent on the distance of the O atoms in the glycol functional group. However, the fluorescence maxima of these new near infrared dyes are practically at same wavelength of the dye of formula 1, i.e. 819 nm. This indicates that only the excitation process has changed, i.e. to what energy level the transition occurs. The lowest vibronic level of first excited state remains unchanged. The absorption maxima of several such esters are: (1) ethylene glycol 796 nm (nanometers); (2) 1,3-Propanediol 780 nm; (3) 1,4-Butanediol 754 nm; (4) 1,6-Hexanediol 744 nm; (5) Triethylene glycol (#4) 790 nm; and (6) IR-144 (R=CH$_2$—CH$_3$) 742 nm.

The modification to 1,3-propanediol is illustrated in equation 1.

In the preferred embodiment, the fluorescence maximum wavelength is about 819 nanometers and the detector is adjusted to receive this wavelength and not others by appropriate filtering. The absorption maxima is selected to be different and to correspond to the preferred available laser diode emission. For example, in formula 1, R may be any of the following four groups, depending on the desired wavelength of the emitted light, which are:

In another embodiment, the infrared dyes are selected to provide at least four dyes with each dye having its exitation and/or radiation spectra spaced sufficiently from each other dye so the flourescence from each dye can be electronically distinguished from each other dye either by the wavelength that excites it into fluorescence or the wavelength at which it fluoresces or both. The spacing is maintained sufficiently close to be excited by laser diodes. The functional groups may be modified as explained above for spacing between the absorption maxima and fluorescence maximum.

In each of the embodiments, the dyes may be incorporated in probes and primers for attachment to oligonucleotides as described in Ruth, Jerry L. (1984) DNA 3, 123. The —OH group provides appropriate linkage to conventional probes by reaction with the appropriate reactive group such as primary amine, carboxylic acid groups and the like but near infrared dyes can be modified to have reactive groups other than the —OH for this purpose.

Figure 1:
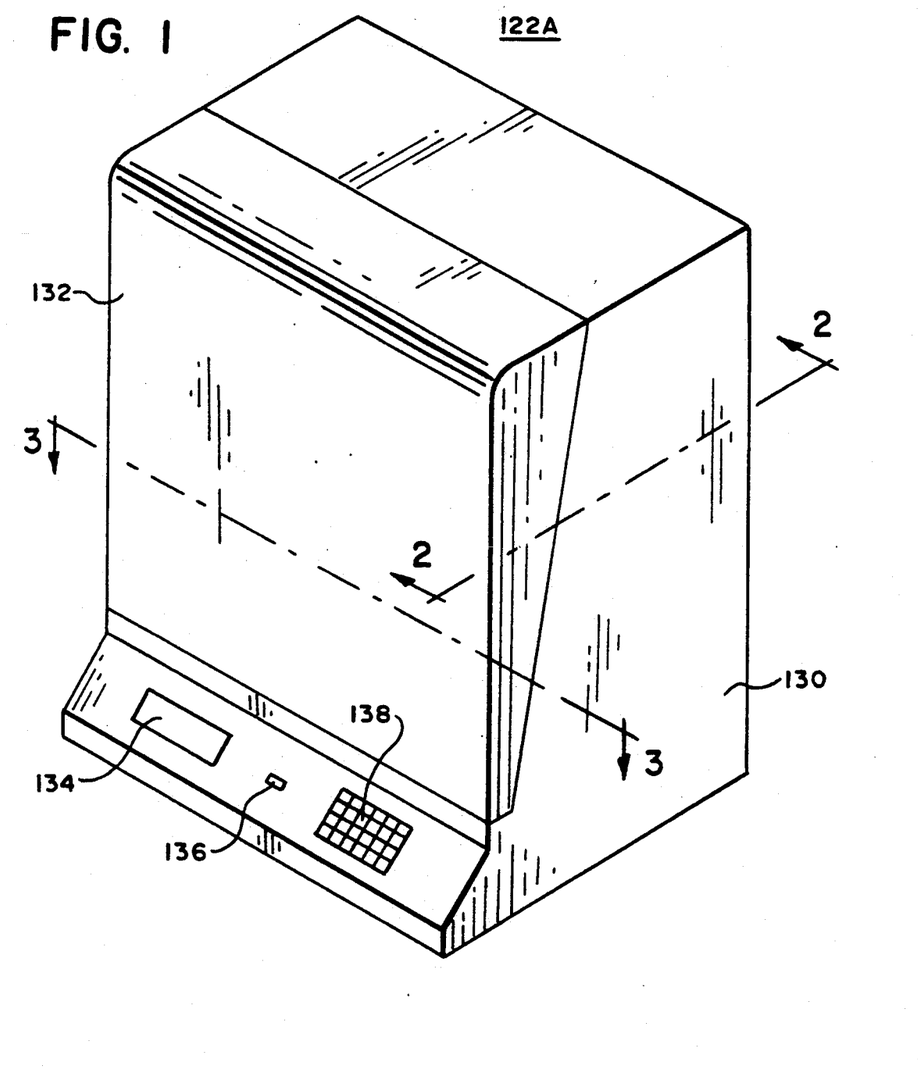
FIG. 1 is a perspective view of an embodiment of sequencer usable in the invention.

In FIG. 1, there is shown a perspective view of an embodiment of sequencer in which the method of this invention may be performed. This sequencer is described in structure and operation in the aforementioned U.S. patent application Ser. No. 07/570,503 filed Aug. 21, 1990; 07/078,279 filed Jul. 27, 1987; and U.S. Pat. No. 4,729,947, all of which are entitled DNA SEQUENCING and which were filed by Middendorf et al. on Mar. 29, 1984.

Figure 2:
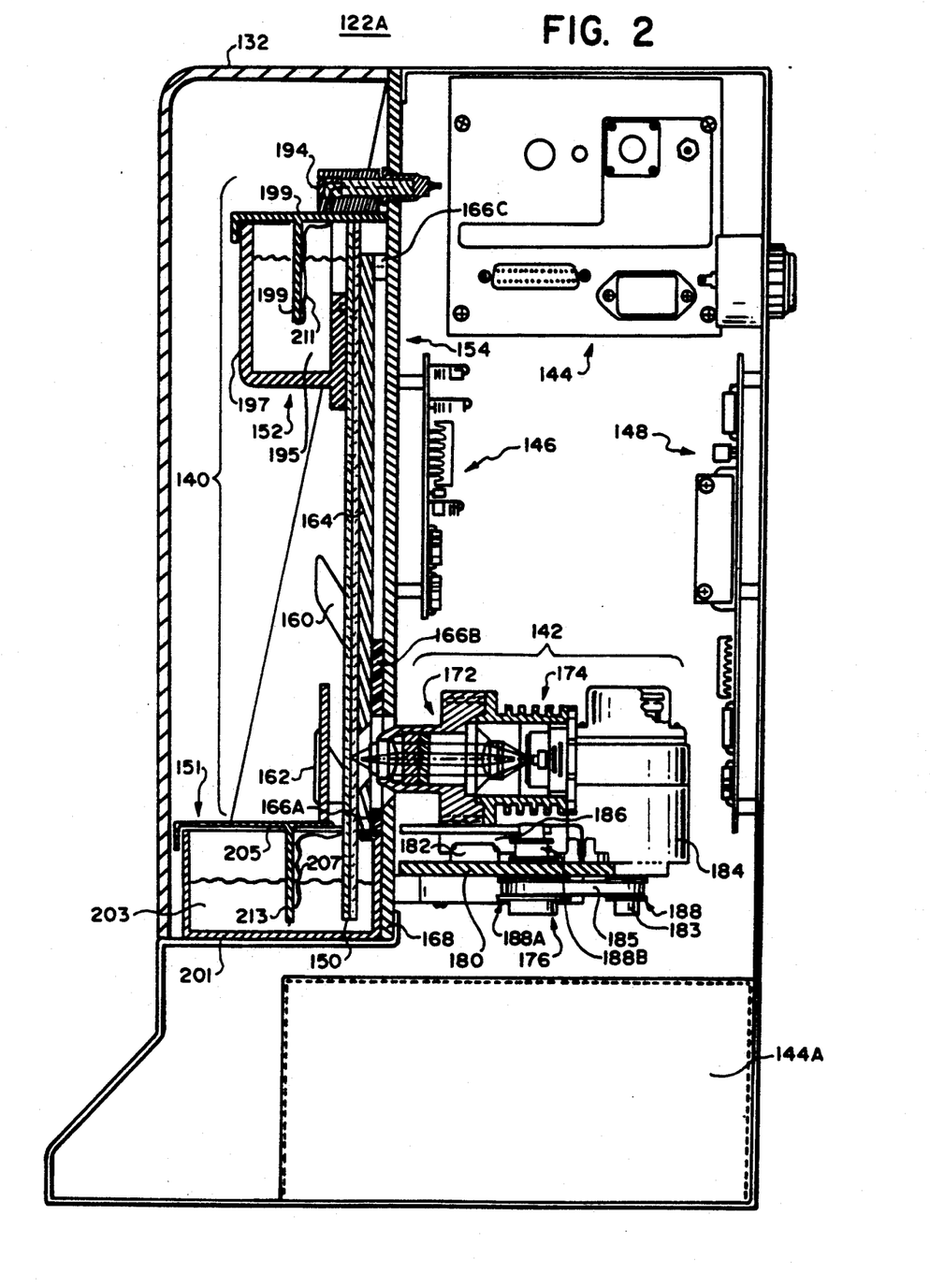
FIG. 2 is a sectional view taken through lines 2—2 of FIG. 1.

In FIG. 2, there is shown a sectional view of the remote station 122A taken through section lines 2—2 of FIG. 1 having an electrophoresis section 140, a scanning section 142, an electrophoresis power supply 144, a system power supply section 144A, an analog board 146 and a digital board 148. The electrophoresis section 140 is positioned near the front of the cabinet and a portion of it is adapted to be scanned by the scanning section 142 in cooperation with circuitry on the analog board 146 and the digital board 148. All of the apparatus are electrically connected to the power supply section 144A for such operation.

To separate different DNA fragments into bands, the electrophoresis section 140 includes a gel sandwich 150, an upper buffer assembly 152, support assembly 154, and a lower buffer assembly 151 positioned to enclose the bottom of the gel sandwich 150. In the embodiment of FIG. 2, the gel sandwich 150 is held substantially vertically and its temperature is controlled during operation. Bands are separated by applying voltage to the upper buffer assembly 152 and lower buffer assembly 151 and scanned by the scanning section 142.

To support the gel sandwich 150, the support assembly 154 includes a pair of upper side brackets and lower side brackets 160 and 162 (only one of each pair being shown in FIG. 2), a temperature control heating plate 164, and a plastic spacer, shown at 166A–166C, in FIG. 2. The entire structure is supported on the support assembly 154 which mounts the upper and lower side brackets 160 and 162.

The upper and lower side brackets 160 and 162 are shaped to receive the gel sandwich 150 and hold it in place in juxtaposition with the scanning section 142. The spacer as shown as 166A–166C space the temperature control heating plate 164 from an apparatus support plate 168 and maintain it at a constant selected temperature above ambient temperature. In the preferred embodiment, the temperature is maintained at 50 degrees Centigrade and should be maintained in a range of 30 degrees to 80 degrees.

The scanning section 142 includes a laser diode assembly (not shown in FIG. 2), a microscope assembly 172, a photodiode section 174 and a scanner mounting section 176. The laser diode assembly (not shown in FIG. 2) is positioned at an angle to an opening in the heating plate 164 so that light impinge s on the gel sandwich 150 to cause fluorescence with minimum reflection back through the microscope assembly 172.

To receive the fluorescent light, the microscope assembly 172 is focused on the gel sandwich 150 and transmits fluorescent light emitted therefrom into the photodiode section 174 which converts it to electrical signals for transmission to and processing by the analog and digital boards 146 and 148 which may provide further analysis of data. The scanning section 142 moves along a slot in the apparatus support plate 168 which is mounted to the scanner mounting section 176 during this operation in order to scan across the columns in the gel sandwich 150.

The scanner mounting section 176 includes a mounting plate 180, a bearing 182, a stepping motor 184, a slidable support 186 and a belt and pully arrangement 185, 188, 188A. The mounting plate 180 is bolted to the apparatus support plate 168 and supports an elongated bearing plate 182, a stepping motor 184 and two pulleys 188 and 188A. The elongated bearing plate 182 extends the length of the gel sandwich 150.

To permit motion of the laser diode assembly (not shown) and microscope assembly 172 with respect to the gel sandwich 150, the slidable support 186 supports the microscope assembly 172 and diode assembly and slidably rests upon the bearing plate 182. An output shaft 183 of the stepping motor 184 drives a pulley 188B through pulley 188, belt 185, and pulley 188A and the pulley 188B drives a belt (not shown) that is clamped to the slidable support 186 to move it the length of the gel sandwich 150 during scanning by the laser diode and microscope assembly 172 which rest upon it. The stepping motor 184 under the control of circuitry in the digital board 148 moves the pulley 188B to move the belt (not shown) and thus cause scanning across the gel sandwich 150.

As shown in this view, the electrophoresis power supply 144 is electrically connected to buffer in the upper buffer assembly 152 through an electrical connector 194 and to the lower buffer assembly 151 through a connector not shown in FIG. 2.

The upper buffer assembly 152 includes walls 197 forming a container to hold a buffer solution 195 and a cover 199 formed with a lip to fit over the walls 197 from the top and containing a downwardly extending flat member spaced away from the side walls and holding a conductor 211. The conductor 211 is electrically connected to the source of power through connector 194 which is mounted to the top of the cover 199 to permit electrical energization of the buffer solution 195.

The bottom buffer assembly 151 includes enclosed walls 201 defining a container for holding a buffer solution 203 and a cap 205 closing the container 201 and having a downwardly extending portion 213 extending into the buffer 203 for supporting a conductor 207 for applying energy to the bottom buffer solution 203. The gel sandwich 150 extends downwardly into the buffer solution 203 and upwardly into the buffer solution 195 to permit the electrical contact for electrophoresis.

Figure 3:
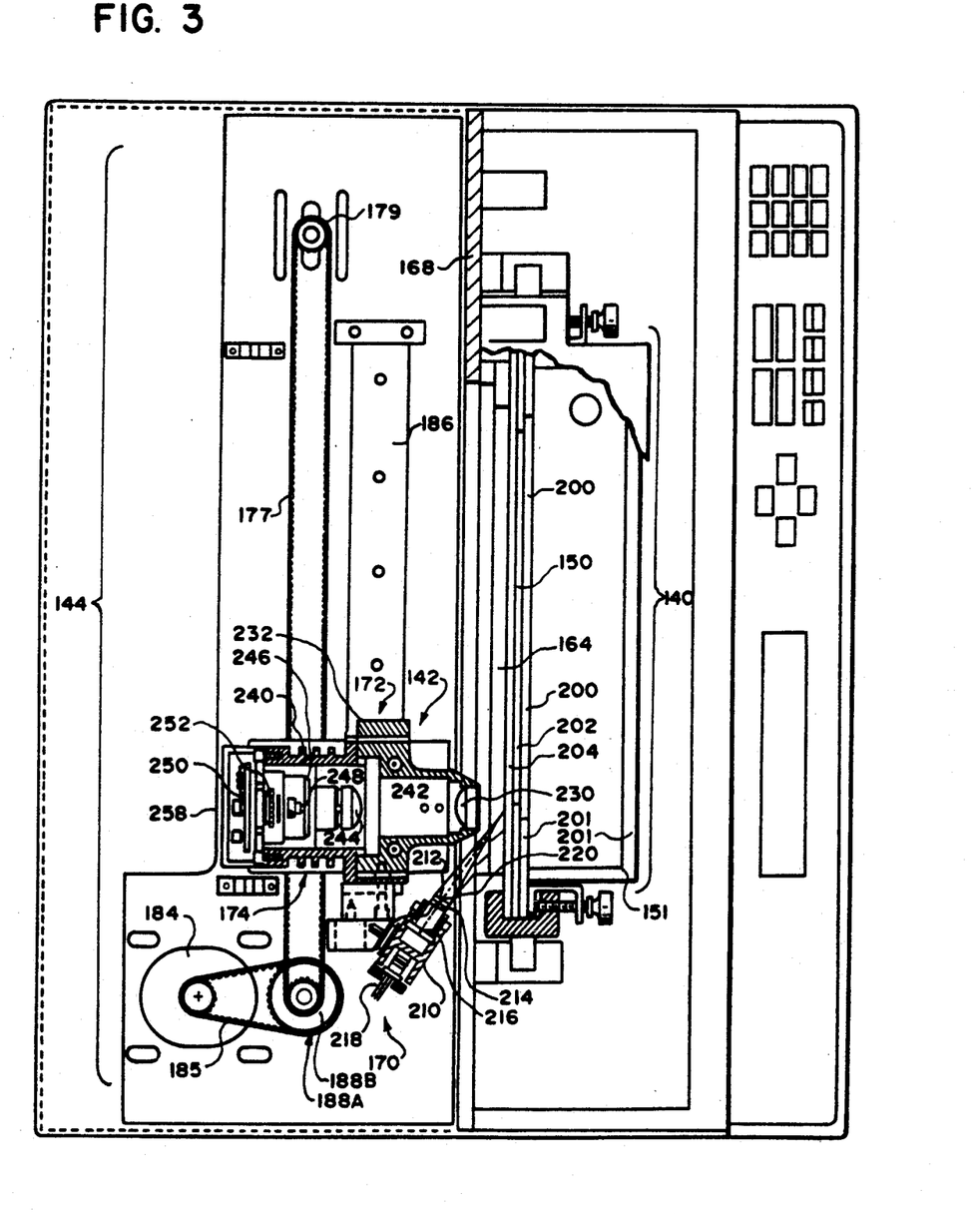
FIG. 3 is a sectional view of a portion of FIG. 1 taken through lines 3—3.

In FIG. 3, there is shown a sectional view taken through lines 3—3 of FIG. 1 showing the electrophoresis section 140, the scanning section 142 and the electrophoresis power supply section 144 mounted together to illustrate from a top view the arrangement of the apparatus support plate 168, the heater plate 164, the gel sandwich 150, a microscope assembly 172 and a photodiode assembly 174. The heater plate 164 and apparatus support plate 168 have slots running in a horizontal direction orthogonal to the lanes of DNA in the electrophoresis section 140 sized to receive the ends of a laser diode assembly 170 and the microscope section 172 for scanning thereof.

To cooperate with the separation and scanning of DNA bands, the gel sandwich 150 includes a front glass plate 200, a gel section 202 and a rear glass plate 204 mounted in contact with the heater plate 164 and having a section exposed for scanning by the laser diode assembly 170 and the microscope assembly 172. The rear glass plate 204 contacts the heater plate 164 and is separated from the front plate 20 by the gel section 202 within which DNA separation takes place. The front and rear glass plates may be any type of glass but are preferably soda lime which has low fluorescence in the infrared and near infrared regions and is prepared by a process that provides optically flat surfaces without grinding.

To transmit light to the gel sandwich 150, the laser diode assembly 170 includes a housing 210, a focusing lens 212, a narrow band pass filter 214, a collimating lens 216 and a laser diode 218. The laser diode 218 emits infrared or near infrared light which is collimated by the laser collimating lens 216 and filtered through the narrow band pass infrared filter 214. This light is focused by the focusing lens 212 onto the gel sandwich 150. Preferably, the point of focus on the gel section 202 of the gel sandwich 150 lies along or near the central longitudinal axis of the microscope section 172 and the photodiode section 174.

The thickness of the glass plates and the gel, the position of the laser and sensor and their angle of incidence are chosen, taking into consideration the refractive index of the gel and glass so that the light from the laser is absorbed by a maximum number of markers for one channel. The light from the laser is not directly reflected back because the angle of incidence to normal is equal to the Brewster's angle at the first interface and is such as to impinge on the markers with full intensity after refraction but not be reflected by subsequent layers of the gel sandwich 150 into the sensor and the sensor views a large number of markers that fluoresce in a line of sight of substantial concentration.

To maintain temperature control over the laser diode, the housing 210: (a) is coupled to a heat sink through a thermal electric cooler 220, and (b) encloses the focusing lens 212, narrow band pass filter 214, collimating lens 216 and laser diode 218; and (c) accommodates the electrical leads for the diode.

To receive and focus light emitted by fluorescent markers from the gel section 202 in response to the light from the laser diode assembly 170, the microscope assembly 172 includes a collection lens 230, a housing 232 and a coupling section 234. The microscope assembly 172 is adapted to be positioned with its longitudinal axis centered on the collection lens 230 and aligned with the photodiode section 174 to which it is connected by the coupling section 234. For this purpose, the housing 232 includes a central passageway in which are located one or more optical filters with a band pass matching the emission fluorescence of the marked DNA strands along its longitudinal axis from the axis of the collection lens 230 to the coupling section 234 which transmits light to the photodiode section 174. With this arrangement, the collection lens 230 receives light from the fluorescent material within the gel section 202 and collimates the collected light for optical filtering and then transmission to the photodiode assembly 174.

To generate electrical signals representing the detected fluorescence, the photodiode assembly 174 includes a housing 240 having within it, as the principal elements of the light sensors, an inlet window 242, a focusing lens 244, a sapphire window 246 and an avalanche photodiode 248. To support the avalanche photodiode 248, a detector mounting plate 250 is mounted within the housing 240 to support a plate upon which the avalanche photodiode 248 is mounted. The inlet window 242 fits within the coupling section 234 to receive light along the longitudinal axis of the photodiode assembly 174 from the microscope assembly 172.

Within the housing 240 of the photodiode assembly 174, the sapphire window 246 and avalanche photodiode 248 are aligned along the common axis of the microscope assembly 172 and the photodiode assembly 174 and focuses light transmitted by the microscope assembly 172 onto a small spot on the avalanche photodiode 248 for conversion to electrical signals. A thermoelectric cooler 252 utilizing the Peltier effect is mounted adjacent to the detector mounting plate 250 to maintain a relatively cool temperature suitable for proper operation of the avalanche photodiode 248.

The lower buffer assembly 151 (FIG. 2) includes outer walls 201 and a bottom wall forming a compartment for buffer solution which encloses the bottom of the gel sandwich 150.

As best shown in this view, the stepping motor 184 rotates the belt 185 to turn the pulley 188A, which, in turn, rotates pulley 188B. The pulley 188B includes a belt 177 extending between it and an idler pulley 179 and attached at one location to the slideable support 186 to move the scanning microscope and laser lengthwise along the gel sandwich 150 for scanning purposes. The motor 184, by moving the carriage back and forth, accomplishes scanning of the gel sandwich 150.

Figure 4:
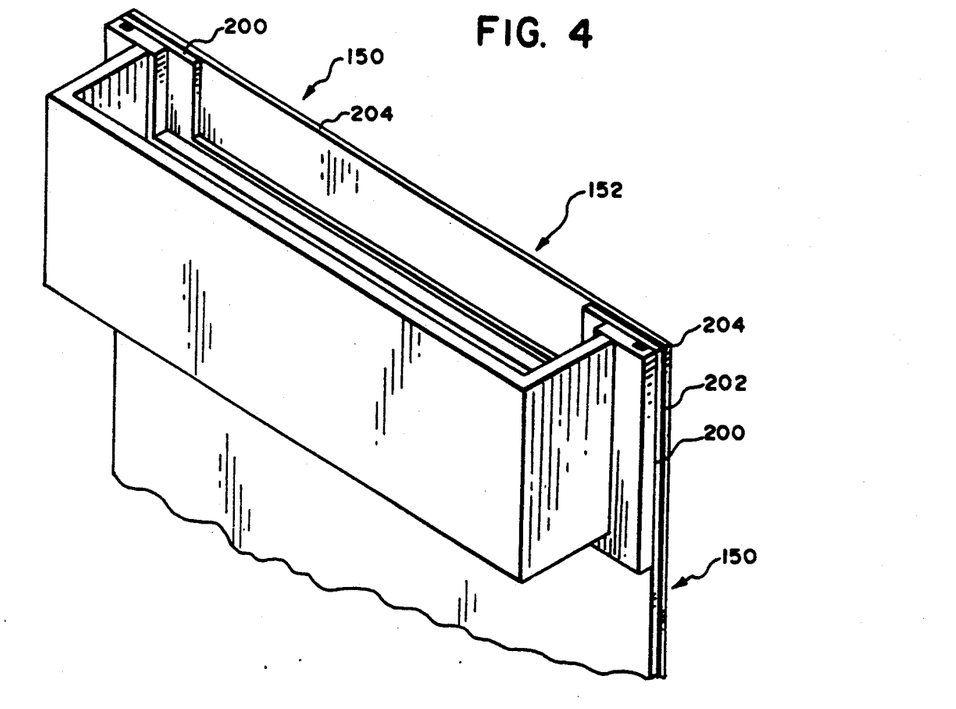
FIG. 4 is an exploded perspective view of a portion of the embodiment of FIG. 2.

In FIG. 4, there is shown a fragmentary perspective view of the gel sandwich 150 and the upper buffer assembly 152 mounted to each other showing the outer glass plate 200 cut away from the rear glass plate 204 to expose the gel section 202 to buffer solution within the upper buffer assembly 152. With this arrangement, samples may be pipetted between the glass plates 200 and 204 and moved downwardly by electrophoresis beyond the upper buffer assembly 152 and through the gel sandwich 150 to the bottom buffer (not shown in FIG. 4).

Figure 5:
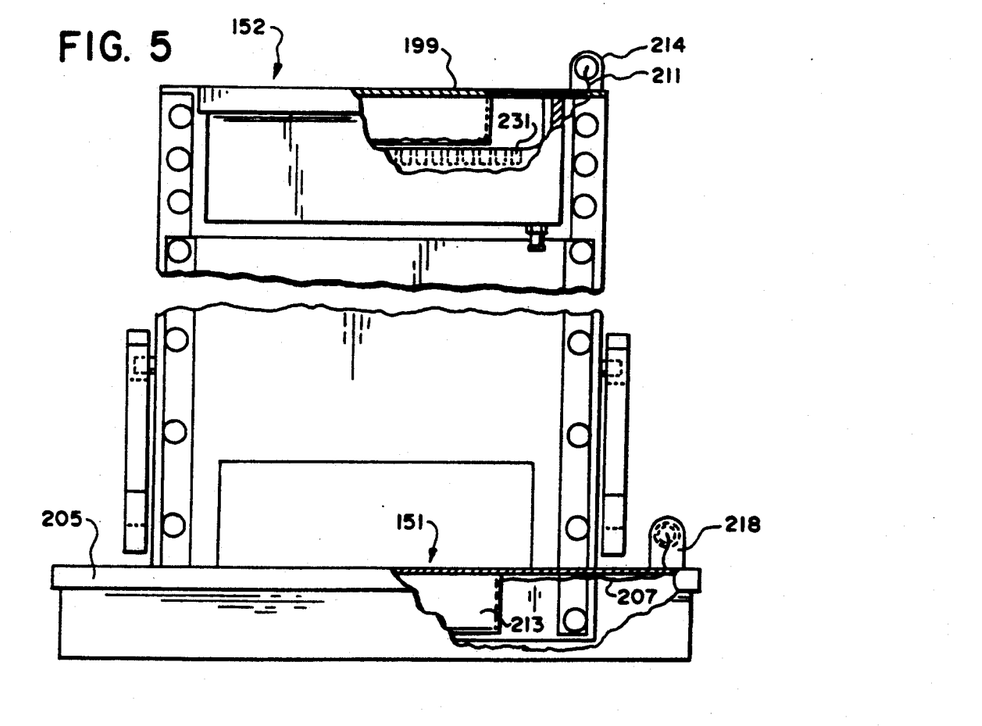
FIG. 5 is an enlarged view, partly broken away, of a portion of the embodiment of FIG. 2.

In FIG. 5, there is shown a broken away view of the gel sandwich 150 illustrating the upper buffer assembly 152 and the lower buffer assembly 151 connected to it at each end. As shown in this view, the cover 199 includes a connecting post 214 which receives the conductor 211 for connection to the downwardly extending portion of the cover 199 into the buffer compartment. Between the glass plates 200 and 204 (FIG. 4) of the gel sandwich 150, are a plurality of downwardly extending recesses 221 in the gel section 202 (FIG. 4) between the plates. DNA sample is pipetted into these recesses to form channels for electrophoresing to the lower buffer assembly 151.

To form an electical connection through the gel sandwich 150 from the upper buffer assembly 152 to the lower buffer assembly 151, a conducting post 216 is connected to the cover 205 of the lower buffer assembly 151 for receiving the conductor 207 which extends downwardly to the downwardly extended plate 213 and into the buffer solution.

Figure 6:
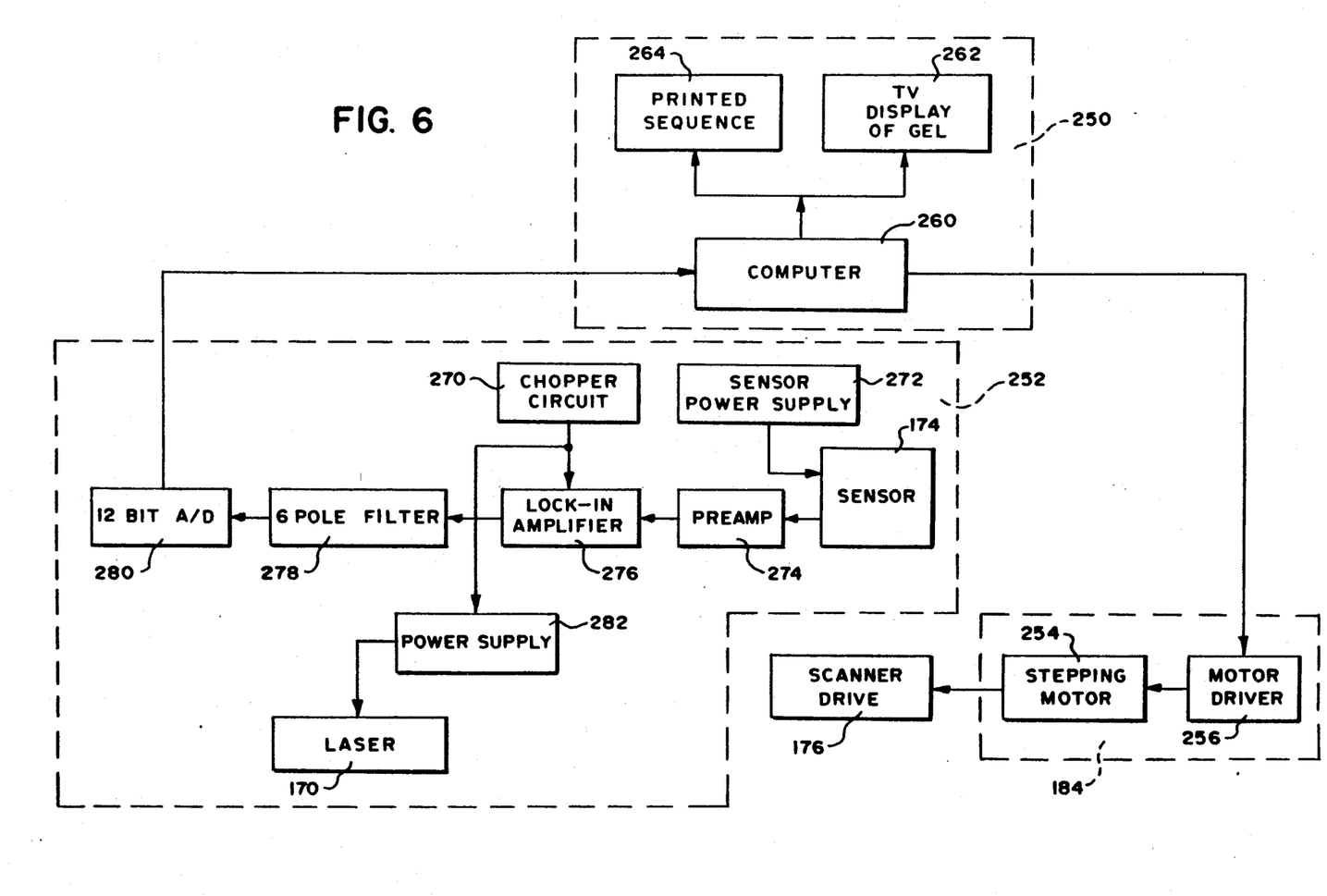
FIG. 6 is a block diagram of a circuit that may be used for coordination of a sensor, scanner drive and laser used.

In FIG. 6, there is shown a block diagram of the circuitry used to control the remote station 122A of the embodiment of FIG. 2 having a control, correlation and readout section 250, the scanner drive 176, the motor assembly 184 for moving the scanner drive 176, and the sensing configuration 252. The sensing configuration 252 includes the laser assembly 170 and the sensor assembly 174 which receives signals, removes some noise, and transmits the signals for display and read out in the control, correlation and read out section 250, while the scanner drive 176 and motor for the scanner drive 184 receive signals from the control, correlation and read out section 250 to control the motion of the sensor back and forth across the gel sandwich. This overall configuration is not part of the invention of this application except insofar as it cooperates with the sensing configuration 252 to scan the DNA and determine its sequence in accordance with the embodiments of FIGS. 1-5.

To drive the sensor 174 from position to position, the motor assembly 184 includes a stepper motor 254 and a motor driver 256. The motor driver 256 receives signals from the control correlation and read-out section 250 and actuates the stepper motor 254 to drive the scanner drive 176. The scanner drive 176 is mechanically coupled to a stepping motor 254 through a belt and pulley arrangement for movement back and forth to sense the electrophoresis channels on the gel sandwich 150 (FIG. 3). The stepping motor 254 and driver circuitry 256 are conventional and not themselves part of the invention.

The control, correlation and read out system 250 includes a computer which may be any standard microprocessor 260, a television display or cathode ray tube display 262 and a printer 264 for displaying and printing the results of the scans.

To sense data, the sensing configuration 252 includes, in addition to the laser 170 and the sensor 174, a chopper circuit 270, a sensor power supply 272, a preamplifier 274, a lock-in amplifier 276, a 6-pole filter 278, a 12-bit analogue digital converter interface circuit 280 and a laser power supply 282.

The sensor 174 receives light from the laser 170 after it impinges upon the gel sandwich 150 (FIG. 3) and transmits the signals through preamplifier 274 to the lock-in amplifier 276. The sensor receives signals from the sensor power supply 272. The chopper circuit 270 provides pulses at synchronized frequencies to the lock-in amplifier 276.

The laser 170 receives power from the power supply 282 which is controlled by the chopper circuit 270 so that the signal from the laser is in synchronism with the signal applied to the lock-in amplifier 276 so that the output from the lock-in amplifier 276 to the 6-pole filter 278 discriminates against unwanted signal frequencies. This signal is converted to a digital signal in the 12-bit analogue to digital converter 280 which serves as an interface to the computer 260.

With this arrangement, the scanning rate may be set to discriminate against noise and the synchronized demodulation from the chopper control further reduces noise, particularly discriminating against the natural fluorescense of the glass in the gel sandwich 150 (FIGS. 2 and 3).

From the above summary, it can be understood that the techniques for the sequencing of fluorescence labeled DNA of this invention have several advantages, such as: (1) because the dyes have their emission spectra in the infrared or near infrared light spectrum, small inexpensive infrared diode lasers may be used; and (2) they are characterized by relatively low noise.

Although a preferred embodiment of the invention has been described with some particularity, many modifications and variations are possible in the preferred embodiment within the light of the above description. Accordingly, within the scope of the appended claims, the invention may be practiced other than as specifically described.

What is claimed is:

1. A method for sequencing DNA comprising:
applying DNA samples marked with fluorescent dye having absorbance and fluorescense maxima at near infrared or infrared wavelengths when combined with the DNA at a plurality of locations in a gel electrophoresis slab for electrophoresing in a plurality of channels through a gel electrophoresis slab;
establishing electrical potential across said gel electrophoresis slab wherein DNA samples are resolved in accordance with the size of DNA fragments in said gel electrophoresis slab into fluorescently marked DNA bands;
scanning the separated samples photoelectrically while they are in the slab with a laser diode and a sensor wherein the laser scans with near infrared or infrared scanning light at a scanning light frequency within the absorbance spectrum of said fluorescently marked DNA samples and sensing light at the emission frequency of the marked DNA;
modulating said light from said laser at a predetermined modulation frequency;
detecting fluorescent light emitted by said DNA bands at said modulation frequency, whereby background noise from the medium through which the light is transmitted may be discriminated against.

2. A method according to claim 1 in which the light is modulated at a frequency within the band between 100 hz to 30 KH.

3. A method according to claim 2 further including means for resolving the bands within at least one channel so that the bands of more mobile strands in the channel are fully resolved while some of the less mobile strands to be later formed into bands are unresolved in a continuous process such that at least 10 percent of the bands are fully resolved while the less mobile strands are yet unresolved into bands in the channel.

4. A method of DNA sequencing comprising the steps of:
applying opposite polarity electrical potentials to a first and at least second buffer;
applying fluorescently marked DNA strands to a plurality of channels of gel, whereby said fluorescently marked DNA is electrophoresed along said gel so that the bands of the more mobile strands in at least one channel is fully resolved while some of the less mobile strands to be later formed into bands are unresolved in a continuous process;
scanning across said channels with light emitted from a laser; and
detecting fluorescent light emitted by said fluorescently marked strands, whereby the time sequence of separated bands may be obtained, wherein the light from said laser is in the band incorporating at least the near infrared and infrared regions and said detector responds to light in a band including at least said near infrared and infrared regions.

5. Apparatus for sequencing DNA comprising:
a gel electrophoresis slab;
means for establishing electrical potential across gel electrophoresis slab;
means for applying DNA samples at a plurality of locations for electrophoresing in a plurality of channels through said gel electrophoresis slab;
means for separating DNA samples in accordance with the size of DNA fragments in said gel electrophoresis slab;
means for scanning the separated samples photoelectrically;
said means for scanning including a laser diode having an emission spectrum that includes one or more wavelengths in the infrared region and near infrared region and a sensor;
a modulator;
a detector being positioned to absorb fluorescent light emitted by said DNA bands;
said sensor being applied to means for detecting pulses of light having the same pulse rate as laser light pulses, whereby background noise from the medium through which it is applied is discriminated against.

6. Apparatus for sequencing DNA according to claim 5 in which said modulator is positioned between said laser and said DNA bands, whereby said light from said laser is pulsed at a predetermined rate, and said scanning apparatus is aligned with said gel, whereby the bands are scanned while still in the gel but after being resolved.

7. DNA sequencing apparatus comprising
gel electrophoresis means;
one end of said gel electrophoresis means communicating with a buffer solution;
at least one other side of said gel electrophoresis means communicating with a second buffer solution;
means for applying opposite polarity electrical potentials to said first and at least second buffer;
means for applying fluorescently marked DNA strands to a plurality of channels of said gel, whereby said fluorescently marked DNA is electrophoresed along said gel so that the bands of the more mobile strands in at least one channel is fully resolved while some of the less mobile strands to be later formed into bands are unresolved in a continuous process;
means for scanning across said channels with light emitted from a laser diode, wherein said light from said laser in in the band incorporates at least the near infrared and infrared regions;
said detector responds to light in a band including at least said near infrared and infrared regions; and
means for detecting fluorescent light emitted by said fluorescently marked strands, whereby the time sequence of separated bands may be obtained.

* * * * *